US010949759B2

(12) United States Patent
Denorme et al.

(10) Patent No.: US 10,949,759 B2
(45) Date of Patent: Mar. 16, 2021

(54) IDENTIFICATION OF A SERIES OF COMPATIBLE COMPONENTS USING ARTIFICIAL INTELLIGENCE

(71) Applicant: OmicX, Le Petit-Quevilly (FR)

(72) Inventors: Marion Denorme, Rouen (FR); Arnaud Desfeux, Sotteville-les Rouen (FR); Emeric Dynomant, Rouen (FR); Fabien Pichon, La Bouille (FR)

(73) Assignee: OmicX, Le Petit-Quevilly (FR)

( * ) Notice: Subject to any disclaimer, the term of this patent is extended or adjusted under 35 U.S.C. 154(b) by 818 days.

(21) Appl. No.: 15/702,879

(22) Filed: Sep. 13, 2017

(65) Prior Publication Data

US 2019/0080250 A1    Mar. 14, 2019

(51) Int. Cl.

| G06N 3/04 | (2006.01) |
|---|---|
| G06N 5/04 | (2006.01) |
| G16B 40/00 | (2019.01) |
| G16B 45/00 | (2019.01) |
| G06N 3/08 | (2006.01) |
| G06N 5/02 | (2006.01) |
| G06F 3/16 | (2006.01) |
| G06F 7/02 | (2006.01) |
| G06T 11/20 | (2006.01) |

(52) U.S. Cl.
CPC ............. *G06N 5/04* (2013.01); *G06N 3/0427* (2013.01); *G06N 3/0445* (2013.01); *G06N 3/084* (2013.01); *G16B 40/00* (2019.02); *G16B 45/00* (2019.02); *G06F 3/167* (2013.01); *G06F 7/02* (2013.01); *G06N 5/022* (2013.01); *G06T 11/206* (2013.01); *G06T 2200/24* (2013.01)

(58) Field of Classification Search
CPC ........................................................ G06N 3/08
USPC ..................................................... 706/15, 45
See application file for complete search history.

(56) References Cited

U.S. PATENT DOCUMENTS

| 2005/0055193 | A1* | 3/2005 | Bondarenko | .......... G16B 50/00 703/22 |
| 2007/0162444 | A1 | 7/2007 | Haselden et al. | |
| 2011/0020320 | A1* | 1/2011 | Gudmundsson | ..... C12Q 1/6886 424/130.1 |
| 2014/0214333 | A1* | 7/2014 | Plattner | .................. G16B 50/00 702/19 |
| 2015/0310163 | A1* | 10/2015 | Kingsmore | ............ G16B 20/00 506/38 |

(Continued)

*Primary Examiner* — David R Vincent
(74) *Attorney, Agent, or Firm* — Morgan, Lewis & Bockius LLP

(57) ABSTRACT

A system, apparatus or process that applies artificial intelligence associated with improved modeling and validation techniques to identify a series of compatible components, e.g., to accomplish an analytical task. In connection with embodiments of the invention, an input module receives input data comprising an inquiry associated with accomplishing a task. A model module receives the input data and designs at least one pipeline comprising a plurality of components designed to accomplish the task. A compatibility module determines at least one valid pipeline by analyzing the at least one pipeline and determining whether each one of the plurality of components are compatible with a component immediately before and a component immediately after the one of the plurality of components. A display module displays the at least one valid pipeline.

24 Claims, 5 Drawing Sheets

(56) References Cited

U.S. PATENT DOCUMENTS

2017/0061070 A1\* 3/2017 Kingsmore ............ G16B 30/00

\* cited by examiner

IDENTIFICATION OF A SERIES OF COMPATIBLE COMPONENTS USING ARTIFICIAL INTELLIGENCE

FIELD OF THE INVENTION

The invention relates to identifying a series of components, e.g., software tools, that may be used in connection with performing a stated task using novel artificial intelligence techniques.

BRIEF SUMMARY OF EXEMPLARY EMBODIMENTS OF THE INVENTION

Embodiments of the present invention relate to improved modeling techniques that may be used to identify a series of components to accomplish a task. In connection with embodiments of the invention, an input module receives input data comprising an inquiry associated with accomplishing a task. A model module receives the input data and identifies at least one pipeline comprising a plurality of components designed to accomplish the task. A compatibility module determines at least one valid pipeline by analyzing the at least one pipeline and determining whether each one of the plurality of components are compatible with a component immediately before and a component immediately after the one of the plurality of components. A display module is displays the at least one valid pipeline.

In some embodiments, the model module identifies at least two pipelines, the compatibility module determines at least two valid pipelines, and one of the at least two valid pipelines is automatically selected and displayed via the display module.

In some embodiments, the model module identifies at least two pipelines and a ranking module is employed to rank the at least two pipelines based on filtering criteria.

In some embodiments, a filtering module is employed and filters components of the at least one valid pipeline based on filtering criteria.

In some embodiments, the model module comprises a neural network trained using a pipeline corpus.

In some embodiments, an end user selects one of the at least one valid pipelines and if the results fits the user's initial request, the selected pipeline is used to train the model module.

In some embodiments, the input data is processed using the input module using natural language processing.

In some embodiments, the input module comprises a chatbox comprising a model based on a recurrent neural network.

In some embodiments, the task is to perform a bioinformatics analysis.

In some embodiments, the components comprise software tools, each software tool having an input format and an output format, and wherein the at least one valid pipeline is determined by analyzing compatibility of the input format of a tool with the output format of the immediately preceding tool in the at least one valid pipeline.

In some embodiments, if the input format is not compatible with the output format, a converter tool is selected to convert one or both of the input format and the output format.

BRIEF DESCRIPTION OF THE DRAWINGS

The foregoing summary, as well as the following detailed description of embodiments of the invention, will be better understood when read in conjunction with the appended drawings of an exemplary embodiment. It should be understood, however, that the invention is not limited to the precise arrangements and instrumentalities shown.

In the drawings.

DETAILED DESCRIPTION OF THE EXEMPLARY EMBODIMENTS

The current invention concerns the domain of a new kind of sorting of lists, specifically of lists composed of tools which can be linked in a complex process. A "tool" is typically a software program or analysis apparatus. The tool may be an industry-specific tool, by way of example.

In some industrial domains, such as the biomedical domain, the number of software tools used in connection with accomplishing a task is extremely large. For example, there are several tools available for a clinician wanting to align genomic sequences to a reference genome.

While many databases of tools exist, they are often difficult to use. Typically, when a clinician selects a specific task (e.g., aligning genomic sequences or quantifying gene transcripts), all tools available for accomplishing the task are displayed when searching a database of tools. There are typically a large number of options and choosing amongst them involves complex decision-making.

In an ideal scenario, the results shown are classified according to tool-specific criteria (e.g. popularity or purchase price of the tool).

However, this approach is unsatisfactory because it does not account for multiple specific steps in the clinician's work. More particularly, when the clinician performs a given task, it is done within the context of a larger study, of which the specific task represents only a very small part. Generally, a first step typically involves data cleaning and quality control and a final step includes data visualization. By way of specific example, following the alignment of genomics sequences (using a first tool), it may be necessary to perform somatic mutation detection analyses (for which a new tool will be necessary).

In addition, any tool used to perform a given task may be compatible with a sub-group of the tools which can be used to perform the next task (i.e., some tools allowing the next task to be done may not be able to accept/interpret the format of the data generated by the first-used tool). If the output data of an initial tool is compatible with the input requirements for a second tool, it is considered that the second tool can be used by means of the output data from the first tool. Such intra-compatible pipelines of tools are referred to herein as "valid pipelines."

By consequence, the simple classification of tools associated with a given task according to a tool-specific criterion (e.g., sorting by increasing purchase price) does not guarantee that the tools available to perform the required task will be compatible.

The current invention presents improvements over prior systems in this and several other regards.

Figure 1:
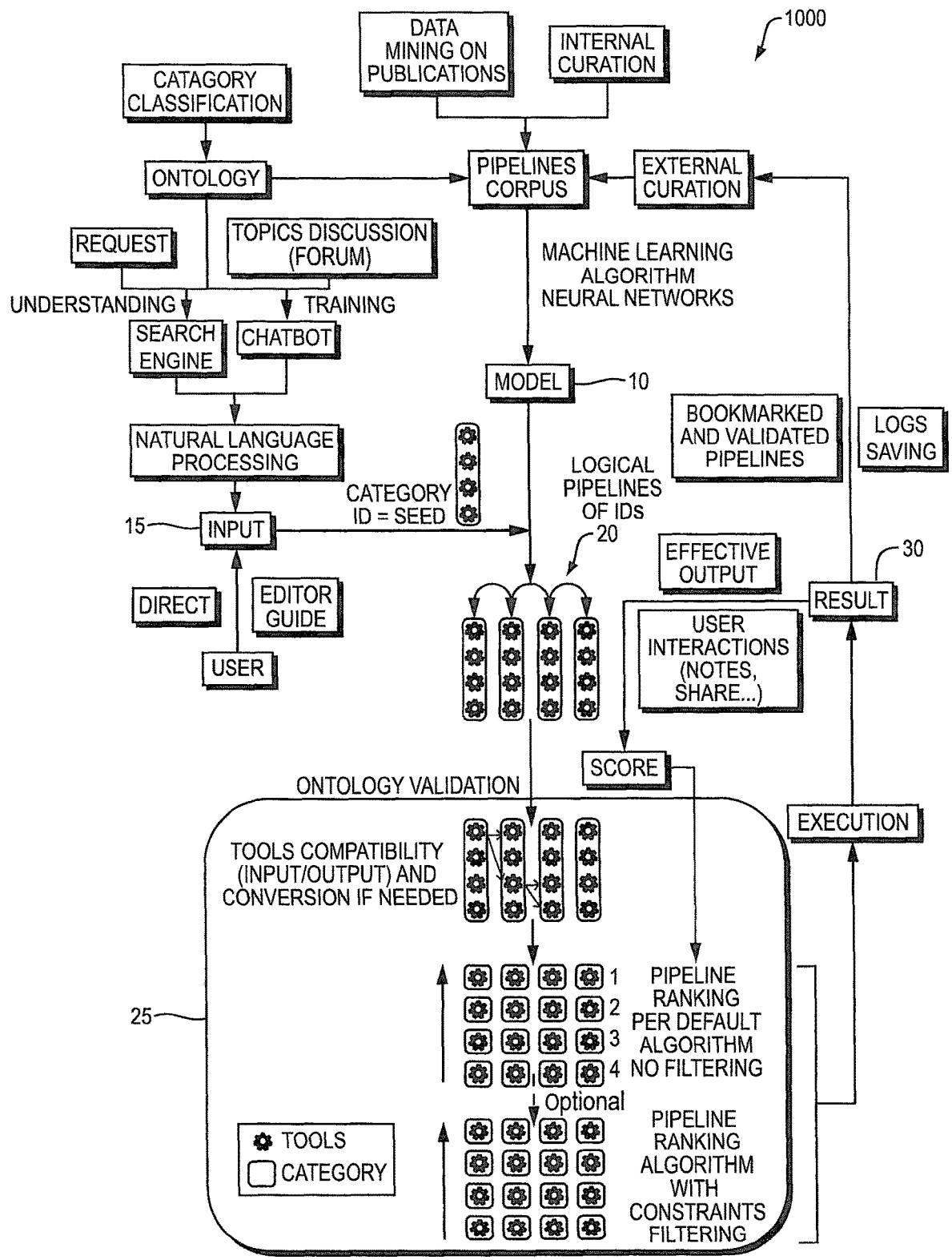
FIG. 1 is a schematic diagram illustrating an overview of the inventive system and method.

As used herein, the term "pipeline" refers to a chain of building blocks/components (e.g., software tools) that are compatible (e.g., output/input compatible) and used in series and/or otherwise in combination to accomplish a goal (e.g., one or a set of tasks, including, by way of example, answering a biological or clinical question). FIG. 1 is a schematic diagram illustrating an exemplary system 1000 and method for carrying out aspects of the present invention. Model module 10 is built by a computer-designed artificial intelligence based on a neural network architecture, trained on a corpus of validated data. Input module 15 comprises a collection of computer components that identify an input and forward it to the model module 10 which generates in turn one or more logical pipelines 20. Compatibility and ranking module 25 comprises a collection of computer components and mathematical algorithms that identify pipelines 20 responsive to an end users query using output/input compatibility criteria, as well as to rank the list of pipelines 20 using filters. Display module 30 receives the ranked results and displays them to the end user. The ranked results may also be used to enrich the pipeline corpus, through externally curated information, as described in more detail below.

Log saving, as referenced in FIG. 1, refers to the fact that the corpus can be enriched, for example, with a direct output of the user if the user saves the pipeline in his profile and by saving an internal log on the server containing end user activity.

Aspects of model module 10 are now described in more detail. The goal of the informatics model 10 is to generate pipelines 20 associated with categories (e.g., groupings of tools that are similarly classified) that are responsive to a specific question (e.g., received through input module 15). In an exemplary embodiment, the pipelines 20 are identified by a list of identifiers (IDs) representing categories. In connection with the model 10, a supervised learning, artificial neural network is built.

The first step is to train the neural network with existing pipelines (also referred to as a pipeline corpus, referred to in FIG. 1). A list of manually-designed or otherwise validated pipelines may be used as training data. Below described are four exemplary ways to generate the pipeline corpus. Other manners of developing training data are within the scope of the present invention.

External curation: Users of the system 1000, an example of which is described with reference to FIG. 1, may create, e.g., via a web application, pipelines for their own use and share the pipelines with other users. Users of the system 1000 may also rate pipelines created or used by other users, or generated by the system, or mark them as favorite. In some embodiments, the most shared pipelines or most marked as favorite may be used as at least part of the pipeline corpus.

Internal curation: Experts in the field, e.g., bioanalysts, may create pipelines by reviewing scientific publications, blogs articles, and books, by way of example.

Data mining on publications: Pipelines may be built by examining (automatically using a computer program) publications that describe tools to accomplish various tasks.

Using an ontology: An ontology may be built that links concepts (instead of words, linked in a terminology) and is used to generate pipelines by permutation of linked terms on the existing ones. For example, if the end user/clinician asks for 'find cancer markers', in an ontology, the concept of 'marker' would be linked to the concept of 'gene expression' or 'circulating tumor DNA' or 'mutation', this last being in turn linked to synonyms like 'variant' and 'SNV' or linked to other concepts like 'INDEL' and 'CNV'. Thus, if an ontology specifically-designed for the classifications is used, categories may be permuted into existing pipelines. In the example provided, the clinician query could be understood as 'find cancer gene expression' or 'find cancer circulating tumor DNA' or 'find cancer variant' or 'find cancer CNV' or 'find cancer INDEL' and return pipelines such as [quality control—gene expression—visualization] and [quality control—circulating tumor DNA analysis—visualization] and [quality control—somatic variant detection—visualization] and [quality control—CNV detection—visualization] and [quality control—INDEL detection—visualization]).

The following continues with an example of the manner in which the model may be trained.

The lists of pipelines, generated in any number of ways as described above, may be vectorized and added to an array. Theses vectors are split, thus extracting lists of category IDs, and a recurrent neural network (RNN) is built. The RNN may be comprised of two hidden layers, in the exemplary embodiment. In some embodiments, a third layer may be included, and provide an ontology-based validation module. Such validation module would improve the artificial intelligence models, as described more fully herein.

The first layer defines many different sliding window sizes for training. So, for example, the first layer draws sliding windows of, e.g., 3, categories and slides with a step of, e.g., 1. These values—i.e., 3 and 1—are provided for ease of explanation; indeed, the hidden layer will generate many different sizes of windows and several different steps to handle a very large amount of data. The result for every pipeline in the training corpus is a set of 3 category IDs vectors (recognizing that 3 is exemplary only and other sizes of windows are within the scope of the present invention).

The second hidden layer computes every probability of having every category ID N in these vectors to be surrounded by the N−1 and the N+1 category ID (and N+x, N−x, depending on the size of the windows).

The output layer pushes in a unique vector for every value for the 3-term vectors composing a pipeline (their number depends on the length of the pipeline, and the number of categories composing it, by way of example). The result is a unique vector, representing every probability for a category to be in a particular place in the pipeline for each pipeline of the training set. Thus, the output layer computes not only the probability of having N between N+1 and N−1 but also to be, e.g., 3-terms far from the N+4 and N−4 terms, assuming 3-term and 9-term windows.

This process is repeated many times, measuring the accuracy and the error rate of the model every certain number of loops by using a small fraction of the training corpus as a validation corpus (e.g., 10-20%). At each iteration of this training, an adaptive learning rate is recalculated according to the accuracy allowing the model to quickly reach a higher maximum accuracy. The model outputs random pipelines and compares them to this validation set. The closer the output pipelines to the validation set, the more accurate is the model. To decrease this error rate, the model auto-adjusts using specifically-designed optimizer functions and an evolving over-loop learning rate until an accuracy as close as possible to 100% is reached, at which point the model may be considered completed.

In one embodiment of the present invention, the results output from this model are analyzed using an ontology to validate output of the model, thereby ensuring pipelines that are functional analytically. This layer of validation added to the artificial intelligence of the model results in an new and improved model, as it ensures better precision, less mistakes and improved quality/reproduction.

In a next step, logical pipelines 20 are generated. The input (received through input module 15) is received by the model module 10. The model uses the input as a seed to build the pipelines in both directions, i.e., by identifying the category used before the category representative of the input/seed (N−1), and the category used after the category representative of the input/seed) (N+1) based on probabilities. The categories identified before and after the input/seed are then included in the loop back to the model and the pipeline continues to be built by extending the pipeline in both directions at the extremities based on probabilities. In an exemplary embodiment, the extensions are stopped by adding an initial value signal as the first step of the pipeline and an end value signal as the last step of the pipeline.

In this manner, lists of logical pipelines (e.g., categories of tools) are generated as a result of the output of the output layer.

By way of an additional explanation, the training data may be composed of sequences of IDs representing categories. The following sequence of IDs is exemplary:

−[0, 796, 841, 587, 265, 3000],

[0, 645, 874, 587, 3000],

[0, 645, 874, . . . ]

with 0 being the start and 3000 being the end signal of a given pipeline. Windows are defined, sliding over the text with a given step (n-Gram technical). For example, if 3-term windows are chosen sliding with a step of 1 term, the following sequences are the result:

[0, 796, 841], [796, 841, 587], [841, 587, 265], [587, 265, 3000], [265, 3000, 3000]

[0, 645, 874], [645, 874, 587], [874, 587, 3000] . . .

Performing this vectorization, the probability of the ID 794 being followed by the ID 841 $P(t+1=841)$ and preceded by the ID 0, $P(t−1=0)$ can be calculated. The probability is calculated for every ID within the pipeline.

By way of further explanation and description, a neural network with two hidden layers can thus be built (e.g., LSTM, Long-Short Term Memory) which computes all calculated probabilities and inserts them into the model. An adaptive learning rate is used during this training to minimize the duration of the training and, ultimately, to achieve more precise results at the end.

The model can be interrogated by an input. In the exemplary case, the input will be the ID of the category answering the complex question asked by the user, which can be obtained through multiple different pathways as described below in more detail with regard to the input module 15.

The model uses the ID of the category as a seed and makes the pipeline to grow around this seed. For example, if the category answering the problem is 874, in the base sequence listed above, this ID is present in pipelines:

[0, 796, 874, 587, 265, 3000]

[0, 645, 874, 587, 3000]

[0, 645, 874, 519, 3000]

...

It can be seen that 874 if often preceded by 645 and followed by 587. As t=874, the model compares every possibility and extracts the most logical for T−1 and T+1. The model has more probability to design during the first step:

[645, 874, 587]

Then, it compares calculated probabilities for 645 and 587 thus having a better chance to design such a pipeline:

[0, 645, 874, 587, 3000]

The program detects that the first ID is 0 and the last ID is 3000, thereby indicating a complete pipeline. By iterating the generation of the ID 874, several pipelines containing the ID 874 can be built, responsive to the initial input. This generating loop can be stopped after a fixed number of pipelines have been designed or run until every possible pipeline has been designed.

In some embodiments, the model is able to predict whether a category is absolutely needed in the pipeline or can be specified as an 'optional category'. Thus, the end user will be able to add, between two mandatory categories, one or several optional categories, thereby providing more possibilities to the pipeline. Theses optional categories will be found by comparing every output from the model. For example, if a category C2 appears between C1 and C3, e.g., in 50% of the valid pipelines, then in pipelines generated by the model 10, the C2 category could be 'optional' between C1 and C3.

Aspects of input module 15 are now described in more detail. Input module 15 receives input directly from an end user, e.g., through a web application, seeking guidance on a particular tool, or set of tools, to use to solve a given problem. Input module 15 may also be used by an end user to indicate tools or pipelines he has used in the past, and/or his favorite pipelines. Some input may be direct and specific (e.g., for advanced users who know what they want). Other input may be interpreted using natural language processing (e.g., to answer a beginner's question, which is likely less precise).

Input to the trained model within model module 10 may be accomplished in several ways. One way may be by inputting an ID directly as described above. In other embodiments, a chatbot may be used. The chatbot may be trained by way of a process that is largely the same as training the model, as described above, except that the chatbot model is trained on text about a specific subject. The model computes the probability of a word being followed and preceded by other words. With a large and specific corpus of training text, the model can be trained to write comprehensive answers and have a discussion with an end user about a subject on which it has been trained, e.g., relating to bioinformatics. Thus, it can be trained to have a conversation with an end user, guiding him to the category that best fits his issue. Following the conversation, through a feedback loop, the chatbot will understand better what the user is looking for. The artificial intelligence comprised within the chatbot thus guides the end user, asking increasingly precise questions, until it fully understands and is able to provide the model with an input (e.g., a category for a specific ID answering user's question). Then, the ID of that category will be known and consumable by the model to identify pipelines that would be suitable for the end user. In a specific example, it is assumed the end user is a beginner in bioinformatics and received transcriptomics sequence data coming from a patient having cancer (i.e., RNA, are representing the step between DNA and proteins). The end user could search relevant tools for: "Find cancer markers". This question is not specific enough to allow a search engine to find a category responsive to the question, as there are many categories relating to cancers and markers. Moreover, markers can be found on DNA, RNA, proteins etc.

To address this problem, a chatbot may be used. An example of conversation with the chatbot follows:

User: Find cancer markers

Bot: What kind of data do you have?

User: I don't know

Bot: Give me the first line of your data file, please

User: Illumina HiSeq 3000/4000—Global run

Bot: It looks like you have NGS data. What did you sequence?

User: mRNA

Bot: So, you want to analyze transcriptomics. What kind of markers do you need?

User: Genes expressed differentially with or without cancer

Bot: I think I just found your starting category for an analysis—Prognostic biomarker identification.

The chatbot model is created to be able to analyze quickly short sentences and build a human-comprehensive answer.

An exemplary manner in which the chatbot model may be trained is now described. Software that implements a sequential model is useful in this context. A sequential model is used when data must be in a logical order in order to be meaningful.

The first step is to build a recurrent neural network (RNN). More specifically, long-short term memory neural networks (LSTM) are particularly good for text sequence generation, because of their ability to keep in memory information for a longer time than other types of neural networks. Thus, they understand better the deep meaning of a sentence by keeping previous words in memory when the analyzing a new one. The RNN implements backpropagation, i.e., information newly calculated impacts information calculated previously. Thus this kind of neural network is fully adaptive.

A multi-layer LSTM is thus used in one embodiment of the invention. The number of hidden layers depends of the size of the training set.

To be able to generate and understand words chains, the model learns vocabulary and grammar specific to the subject. For example, a forum, such as a website, about bioinformatics questions/answers would form an ideal corpus set.

Training the model will enable it to calculate probabilities of: a word being followed by another word for all words in the training set; and a character being followed by another character, including punctuation. This information may be stored into multi-dimensional arrays, which allows for fast calculations.

Compatibility and ranking module 25 is now described in more detail.

The model, trained on the corpus of pipelines, outputs sorted and logical lists of categories as in the example below:

{0, 794, 811, 224, 72, 3000}
{0, 794, 541, 623, 72, 3000}
{0, 541, 623, 587, 3000}

Each of these options is responsive to the original question input by the user. In a given category (represented by Cx), many tools IDs CxTy belong to this category. A matrix (M1) can be set up, e.g., as follows:

| $C_{794}$ | $C_{811}$ | $C_{224}$ | $C_{72}$ |
|---|---|---|---|
| $C_{794}T_1$ | $C_{811}T_1$ | $C_{224}T_1$ | $C_{72}T_1$ |
| $C_{794}T_2$ | $C_{811}T_2$ | $C_{224}T_2$ | $C_{72}T_2$ |
| $C_{794}T_3$ | $C_{811}T_3$ | $C_{224}T_3$ | ... |
| $C_{794}T_4$ | $C_{811}T_4$ | ... | |

Many combinations of tools are possible and responsive to the original question input by the end user. Also, a tool can be used in many chains.

Nonetheless, in connection with generating a pipeline, the format of the output of one tool must be compatible with the input format of the following tool. For example, the output of tool X is an X file, which is also the input to tool Y. Thus, tool Y can be run after tool X, but the opposite is not true. Input and output of each of the tools are thus compared to ensure that the outputs and inputs are compatible and that the pipeline can be run without a failure. In this sense, if a mismatch occurs, the algorithm will try to find a converter in the system database. If such a converter is found, it may be proposed automatically in the pipeline. If not, the pipeline is removed from the list of proposed pipelines.

Thus, the first step is to check compatibility between a tool and the following or the precedent tool in the list. By taking, the C811T3 as example, its input data will have to be the same format as the output of the tool coming from C794 and its output data format will have to be the same as the input of the C224 tool. Thus, knowing the input and the output of every tool, it is checked if the C811T3 is compatible with:

$C_{794}T_1$ or $C_{794}T_2$ or $C_{794}T_3$ or $C_{794}T_4$ $C_{794}T_x$ for its input and $C_{224}T_1$ or $C_{224}T_2$ or $C_{224}T_3$ ... $C_{224}T_x$ for its output.

If a backward or a forward compatibility is detected between two tools, a link is established between them. This verification extends in both directions, until it reaches an end of the list. Tools that are not compatible are removed, i.e. leading to matrix (M2).

The horizontal chaining of the following matrix (M2) thus respect the equality (see the equation below). More particularly, tools are vertically chained in the matrix depending on the category to which they belong. Thus, tools appear under their category. But in the matrix shown below, the tools are also compatibles in every row, i.e., output from C794T1 is the same than C811T2 and C811T3 because it is on the same row as both C811T2 and C811T3. The compatibility checking algorithm designed all possible chains.

$$OC_{N-1}T_x = I\ C_N T_y$$

$$OC_N T_y = I\ C_{N+1} T_z$$

With:

O (Output), I (Input), $C_N$ (Category N), $T_x$ (Tool x)

| $C_{794}T_1$ | $C_{811}T_2$ | $C_{224}T_1$ | $C_{72}T_3$ |
|---|---|---|---|
| $C_{794}T_1$ | $C_{811}T_2$ | $C_{224}T_1$ | $C_{72}T_3$ |
| $C_{794}T_1$ | $C_{811}T_3$ | $C_{224}T_2$ | $C_{72}T_3$ |
| | | ... | |
| $C_{N1}T_{x1}$ | $C_{N2}T_{x2}$ | $C_{N3}T_{x3}$ | $C_{N4}T_{x4}$ |

Here again, validation using an ontology layer may be employed. Thus, if a non-logical pipeline is designed by the artificial intelligence (e.g, a graph generation step showing up before the end of the process to get the final result), it could be deleted (if the different steps are not analytically compatible) or re-organized (it only the order of the steps is problematic). By adding this verification step, the computational design of models is improved.

Next, ranking algorithms may be employed. In a first embodiment, end users do not use any filters and, in this embodiment, intra-compatible pipelines are ranked using the following described algorithms A score for each tool included in the pipeline will be calculated, and the sum of the scores is divided by the total number of tools included in the pipeline (i.e., the mean of the scores of tools included in the pipeline). Each parameter is weighted in agreement with the importance given to the parameter. Examples of parameters used in the score calculation are (ordered by importance in an exemplary embodiment): the average rating of the tool by end users; a number of article citations of the tool by a relevant publication; a number of publications for this tool; a number of reviews of the tool by end users; a number of times the tool has been indicated as a favorite by end users; whether the tool has documentation; whether the tool has a video explaining its use; the year of the tool's first publication and last publication; a number of comments on the tool by end users; whether the tool is available online; and whether tool continues to be maintained. Such parameters are exemplary only; more or fewer parameters may be used within the scope of the present invention. In an exemplary embodiment, the tools once scored are formatted for displayed in a decreasing score order, the most efficient and popular tool being the first of the list.

The following provides an exemplary formula that may be used to calculate the score for a tool:

Score=Average Review(if Review=0 or Review=3, then score=0; if Review<3, then score=−12/Review; if Review>3, then score=Review*3)+Date of last publication(score=max(publication year−current year, −4))+Date of first publication (if publication: score=0 else score=−1)(e.g., if there is a publication about the tool, the score for this parameter is zero; if there is no publication at all, the general score will decrease)+Number of Publications(score=publication number)+Citations(if citations: score=2*LOG(total number of Citations)else score=−1*Number of publications)(e.g., if the tool has been cited in other studies, indicating that it has been previously used by other scientists, the score is equal to 2*log(citations); if it has not been cited (=else),the score is equal to the number of publications about the tool)+Availability(if link OK: score=0 else score=−500)+Obsolete(if tools still maintained: score=0 else score=−500)+Number of reviews(score=Number of reviews/2)+Number of comments(score=Number of comments/100)+Documentation(if documentation: score=2 else score=0)

The mathematical notation for calculating the score follows (assuming 11 scores are calculated):

$$Score_{tool} = \sum_{parameter=1}^{11} Score_{parameter} \text{ with:}$$

$Score_{AverageRating}$=if no rating or average rating=3, then $Score_{AverageRating}$=0; if average rating<3, then $Score_{AverageRating}$=(−12/average rating); if average rating>3, then $$Score_{AverageRating} = (\text{average rating} * 3)$$

$Score_{LastPublication} =$ (last publication year − current year) with $\max(Score_{LastPublication}) = -4$ $Score_{FirstPublication}$ = {if publication:$Score_{FirstPublication}$ = 0;

if no publication:$Score_{FirstPublication}$ = −1}

$Score_{TotalPublications}$ = Total number of publications about this tool $Score_{Citations}$ = {If tool has been cited:$Score_{Citations}$ =

2*LOG(total number of citations); if not cited in other articles, $Score_{Citations}$ = −1*Number of publications written about the tool $Score_{Availability}$ = if tool link is not in 404 error:$Score_{Availability}$ = 0;

if it is:$Score_{Availability}$ = −500

$Score_{Obsolete}$ = if tools is still maintained:$Score_{Obsolete}$ = 0;

if deprecated $Score_{Obsolete}$ = −500

$Score_{NumberOfRates}$ = (number of ratings/2)

$Score_{NumberOfComments}$ = (Number of comment/100)

$Score_{Documentation}$ = (if documentation available:$Score_{Documentation}$ = 2, if not:$Score_{Documentation}$ = 0)

In a specific example, assuming the tool X has: an average rating of 4.5 (from with 37 different ratings) and has been commented on 124 times; developers have written 7 publications about 7 versions release of this tool, between 1999 (first release) and 2016 (version 7). The cumulated number of citations for its 7 publication is 3254. The Internet link on to the tool X webpage is functional; this tool is still maintained and a well-written documentation is available online. Thus:

ScoreAverageRating=4.5*3=13.5
ScoreNumberOfRates=37/2=18.5
ScoreNumberOfComments=124/100=1.24
ScoreAvailability=0
ScoreObsolete=0
ScoreDocumentation=2
ScoreLastPublication=2016−2017=−1
ScoreFirstPublication=0
ScoreTotalPublications=7
ScoreCitations=2*log(3254)=7.02
Thus ScoretoolX=(13.5+18.5+1.24+0+0+2−1+0+7+7.02)=48.26.

This score of 48.26 will be automatically ranked according to other tool's scores. Thus, pipelines are output/input compatible and ranked, without any action from the user. In another embodiment, the user has selected filters in connection with selecting specific tools. In this embodiment, a score is calculated for every tool of the pipeline with the algorithm below and then the mean function is applied by summing the score of each tool in the pipeline and dividing by the number of tools in the pipeline.

A list of filters is then applied to the matrix containing all possible pipelines of inter-compatible tools. Theses filter are considered as boolean variables, i.e., having two possible values: 0 (the tool doesn't pass the filter) or 1 (the tool passes the filter). The end user may select filter values directly by indicating the same in a user interface. For example, if the user only clicks on the "basic" box, every tool considered "basic" (i.e., not complex) will have a score of 1 for this filter.

For continuous variables, the user may select a minimum and a maximum. If the tool value is between the minimum and the maximum, the tool will have a score of 1 for this filter.

Thus, for every tool from the M2 matrix, a filtering score is calculated, using a matrix (M3) with a number of rows equal to the number of single tools and a number of columns representing the number of filters. For example, the following matrix represents X tools and 12 filters.

|  | $F_1$ | $F_2$ | $F_3$ | $F_x$ | $F_{12}$ |
| --- | --- | --- | --- | --- | --- |
| $C_{794}T_1$ | 0 | 1 | 1 |  | 0 |
| $C_{811}T_2$ | 0 | 1 | 1 |  | 1 |

-continued

|         | $F_1$ | $F_2$ | $F_3$ | $F_x$ | $F_{12}$ |
|---------|-------|-------|-------|-------|----------|
| $C_{811}T_3$ | 1 | 0 | 1 |  | 0 |
| ... |  |  |  |  |  |
| $C_N T_x$ | 1 | 1 | 1 |  | 0 | with $F_x$ being the filter number x.

For every row, a tool score value is calculated as follows:

$$S_{C_N T_y} = \sum_{x=1}^{12} \Phi_{F_x} \text{ with } \begin{cases} O_{C_{N-1} T_x} = I_{C_N T_y} \\ O_{C_N T_y} = I_{C_{N+1} T_z} \end{cases}$$

With CN (Category N), Ty (Tool y), ΦFx (score 0 or 1 for filter x), O (Output), I (Input).

Every tool has a score ranging from 0 (matching 0 filters) to X (matching every filter, which is 12 in the above example). This score can thus be substituted for the ID CN Tx of each tool in the matrix M2 to create a matrix (M4). Then, this matrix M4 is vertically sorted.

Then, score values for a given pipeline are summed, and the sum is divided by the number of tools to determine the mean. Each output/input compatible pipeline can then be ranked as a function of the filters chosen by the end user.

These algorithms may be implemented in an informatics computer program, using, for example, Python as a language with appropriate libraries for matrix math operations and logical model building.

Thus, with reference again to FIG. 1, tools are tested for compatibility to generate intra-compatible pipelines of tools belonging to categories chaining generated by model 10. The pipelines are then ranked with (i) no filters selected by the end user (in which case ranking occurs with reference to, e.g., publications and activities relating to the tools) or (ii) with end user selected filter activated, in which case ranking occurs with reference to matching filters. The final goal of these ranking is to output at least the best pipeline for the user.

The output of compatibility and ranking module 25 is launched and displayed to the end user through a display module 30, e.g., on a web interface. The end user's ultimate choice of pipeline, as well as any favorites indicated by the end user, may be fed back into the system and used to calculate the score, as described in more detail above. Thus, for example, if the end user is not satisfied with the proposed pipeline, the information may be entered back to the model and the weight for the specific combination of programs will decrease, thereby improving the model. If the pipeline is satisfactory as answering the initial question, and chosen by the end user, it will be added to the training corpus as an externally curated addition. The weight of these pipelines in the model's training may be weighted slightly less than pipelines identified in scientific literature, but they are taken into account to some extent, in an exemplary embodiment.

Figure 2:
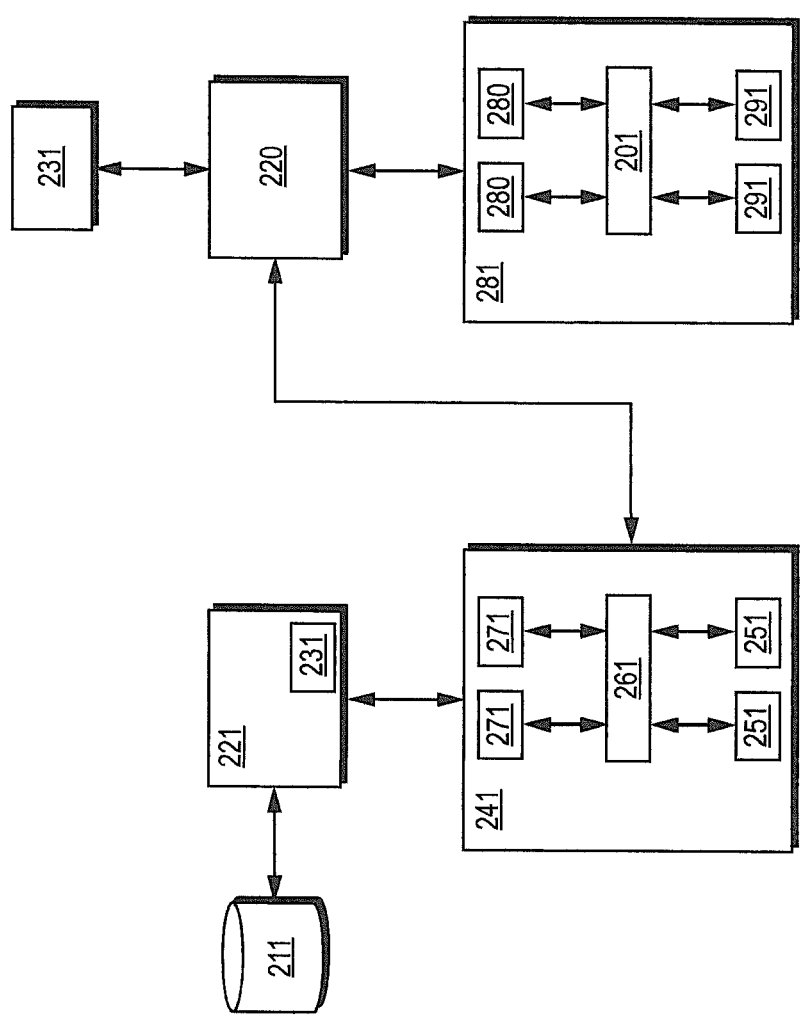
FIG. 2 illustrates an exemplary computer system for carrying out aspects of the present invention.

In some embodiments, the methods are carried out by a system that employs a client/server architecture such as, for example, the exemplary embodiments described as follows with reference to FIG. 2. The data that may be used as an input to the system and the outputs from the system(s) may be stored in one or more databases 211. Database server(s) 221 may include a database services management application 231 that manages storage and retrieval of data from the database(s) 211. The databases 211 may be relational databases; however, other data organizational structures may be used without departing from the scope of the present invention.

One or more application server(s) 241 are in communication with the database server 221. The application server 241 communicates requests for data to the database server 221. The database server 221 retrieves the requested data. The application server 241 may also send data to the database server 221 for storage in the database(s) 211. The application server 241 comprises one or more processors 251, non-transitory computer readable storage media 271 that store programs (computer readable instructions) for execution by the processor(s), and an interface 261 between the processor(s) 251 and computer readable storage media 271. The application server 241 may store the computer programs and code used to implement the methods of the present invention.

To the extent data and information is communicated over a network (e.g., the Internet or an Intranet), one or more network servers 281 may be employed. The network server 281 also comprises one or more processors 291, computer readable storage media 280 that store programs (computer readable instructions) for execution by the processor(s), and an interface 201 between the processor(s) 291 and computer readable storage media 280. The network server 281 is employed to deliver content that can be accessed through the communications network 220, e.g., by an end user employing computing device 231. When data is requested through an application, such as an Internet browser, the network server 281 receives and processes the request. The network server 281 sends the data or application requested along with user interface instructions for displaying an interface on device 231, which may be an end-user computer, mobile phone, or tablet, by way of example.

The computers referenced herein are specially programmed to perform the functionality described herein.

The non-transitory computer readable storage media (e.g., 271 or 280) that store the programs (i.e., software modules comprising computer readable instructions) may include volatile and non-volatile, removable and non-removable media implemented in any method or technology for storage of information such as computer-readable instructions, data structures, program modules, or other data. Computer readable storage media may include, but is not limited to, RAM, ROM, Erasable Programmable ROM (EPROM), Electrically Erasable Programmable ROM (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the computer system and processed.

Each of the computer modules described herein are specially programmed to implement the functionality described herein.

Once the pipelines are built, an end user may then employ the system. Exemplary user interfaces are now illustrated with reference to FIGS. 3a through 3c. Such interfaces may be displayed on an end user device, such as a computer, mobile phone, tablet, or other computing device.

Figure 3A:
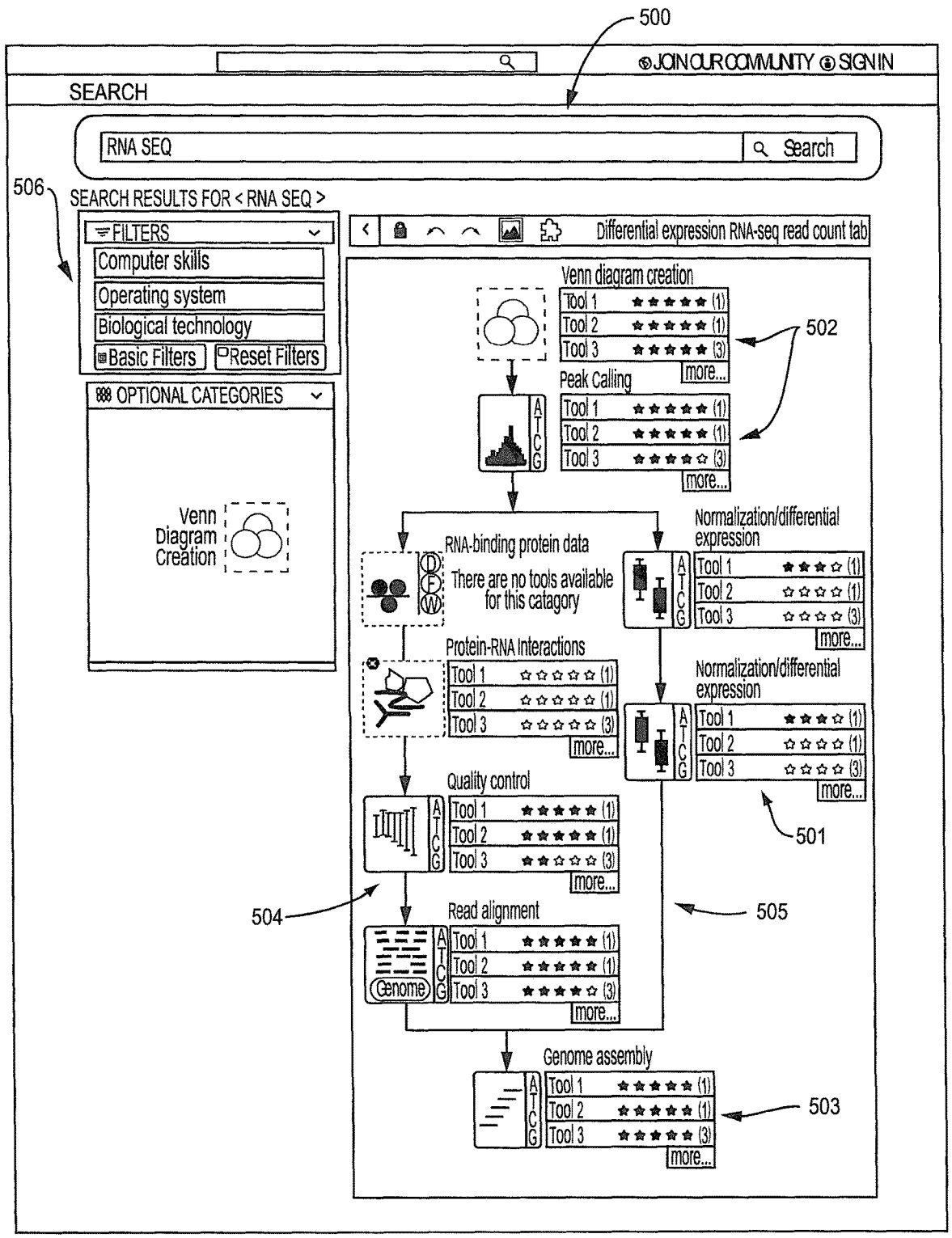
FIG. 3a through 3c are exemplary user interfaces that may be used to access the functionality of an exemplary embodiment of the invention.

With reference to FIG. 3a, an end user may input a query into search box 500. In this example, the end user inputs "RNA seq", a type of gene-expression analysis. The system 1000 (referenced in FIG. 1), searches the database using this keyword and extracts the relevant pipeline, displaying it in display area 501. In this example, two categories 502 are returned, representing the steps in the analysis (i.e., Venn diagram creation, and peak calling, in this example). As can be seen in this example, two possible paths (path 504 and path 505) are possible to reach the final step 503 of genome assembly. The presented pipelines have been chosen based on output/input compatibility and the first ranking algorithm, as described more fully elsewhere herein (it is noted that the pipeline provided in this example is exemplary only).

Figure 3B:
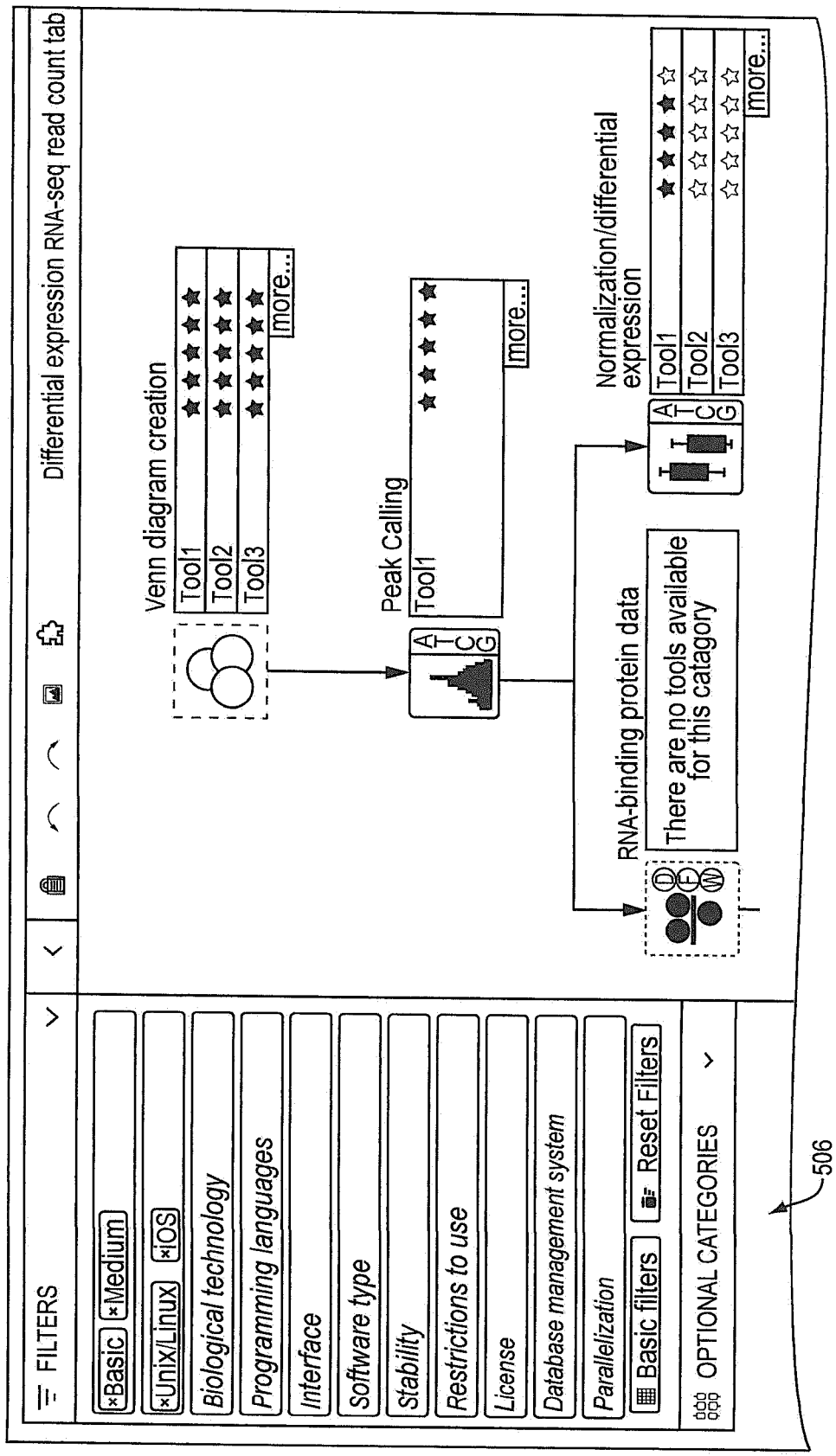
Figure 3C:
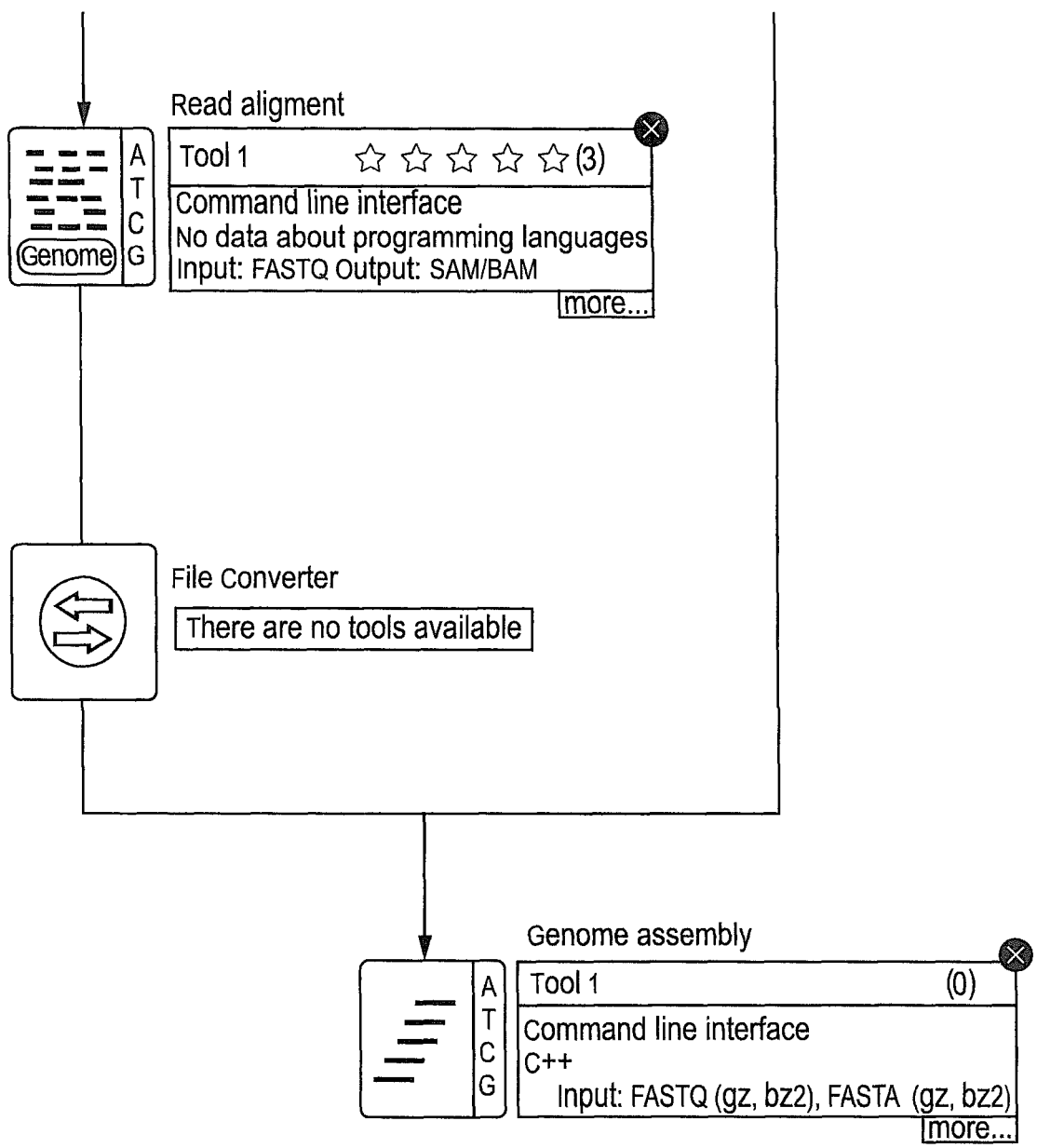

As shown in FIG. 3*a*, as well as FIG. 3*b*, filters 506 may be employed (i.e., to perform the second ranking procedure, as described more fully herein). More particularly, under each category, tools associated with the step are listed. The tools are ranked using, e.g., the algorithm described above, and may be filtered using filters 506. Thus, for example, the filters allow the end user to indicate that he does not want to work with advanced tools (and, thus, basic and medium tools are selected), and wants to work with UNIX-core machines (and, thus, Linux is indicated). Other filters may be selected within the scope of the present invention. Once applied, it can be seen that the tools within each of the categories have changed to reflect the tools available that meet the filters.

In other embodiments, the best tool in each category may be displayed, in accordance with the assigned score. Filters may also be employed in this embodiment as well.

In some embodiments, a conversion functionality may be used, e.g., to resolve the problem of output/input compatibility between tools. For example, if the user selects, via auto-completion or manually, two tools with no compatibility, a file converter appears to adapt the output of the format of the first tool to an acceptable input format of the second tool. Such functionality is illustrated with reference to FIG. 3*c*.

In still other embodiments, optional steps are made available. In this case, a category may be displayed in a lateral bar and the end user can, by drag and drop, place the category into the pipeline, between the two steps surrounding the optional step.

A computer system is required to perform the processes described herein. For example, there are a large number of potential tools, and associated categories, that are potentially responsive to a user's inquiry. In addition, there are a variety of filters that may be applied, each of which will have multiple associated values. Further, there are a number of tools per pipeline. Factoring in all of these variables, the number of possible combinations of categories, tools and filter values, the number of potentially available pipelines to be analyzed for responsiveness to an end user inquiry is extremely large. Thereafter, the output/input compatibility between the tools must be determined, and rankings must be determined. The foregoing analysis is impossible for a human to implement on a realistic scale, let alone with any consistency of outcome.

While the exemplary embodiments are described herein with reference to bioinformatics, aspects of the present invention are useful in a variety of contexts. For example, aspects of the present invention may be used in connection with an improved search engine. In known search engines, the end user inputs one or more keywords, returning a list of media or documents linked to the subject, depending on the precision and recall score of the search engine. Aspects of the present invention may improve this process. More particularly, if each resource on the web (e.g., texts, videos, images, etc.) is categorized according to specific terminology, e.g., for World War H History, each resource content may be tagged with controlled relevant vocabulary, e.g., year, duration, and country, which would serve as the filters employed in connection with the present invention.

Continuing with this example, if the query of the user employing the computer system of the present invention is "What was the WW2 curse?", for example, the result would be a list of temporally-sorted terms extracted from the ontology linked to the keyword "WW2" identified by the natural language processor:
   Category 1: Hitler's rise to power
   Category 2: Poland invasion.
   Category 3: Holocaust
   Category 4: . . .
   Category X: Liberation, of Europe The compatibility between these media results could also be checked. For example, the system would avoid chaining a video with text and, instead, produce logically ordered lists of different relevant media. The media may be first filtered on different subjects (e.g., year, duration, country, language, author, editor) and then ranked, e.g., using the number of visits by end users to the web pages composing the list. Lastly, the sequence selected by the user is added to the corpus and used to continue to train the model. The result for a search engine employing aspects of the present invention is, thus, not only a vertical list of media, but a list of horizontal lists, logically sorted and using the same media type.

In another example, each course offered by a university may be categorized according to educational subjects, and each course may be tagged with controlled vocabulary, e.g., level, start and end, credits, and price. Thus, instead of choosing a university course by subject, like "biology" or "art", students could choose using a more powerful tool. University programs are vertical, chaining year N−1 with N and N+1. For example, the query could be "I want to work on data science for the NASA." The input, received through a natural language processing engine, may comprise important aspects of the school programs (e.g., astrophysics, computing science and mathematics, in this example). The model then builds a logical order of courses to follow, representing every semester (e.g., or months, or years) as follows:
   Category 1: Mathematical basics
   Category 2: Computing science for beginners
   Category 3: Astrophysics lvl 1
   Category 4: . . .
   Category X: Mathematical advanced In this example, the student must take basic math and computing science before astrophysics (following output/input compatibility). In addition, it may be that the student must achieve certain, grades in a pre-requisite course before being able to take the next course. Filters could be applied relating to geographic distance of the university from a given point A or relating to cost, by way of example. The result of the processing is a personalized syllabus for the student according to his location, his revenues and even his skills. In the event it is determined that the student has not achieved a sufficient level to follow a specific course, the system may automatically propose in the syllabus a refresher course to bring the student up to standards. Thereafter, the result of this program could be measured by, e.g., the time needed for the graduate student to find a job, his salary, etc. to assess the effectiveness of the program, feed the result back into the model for training purposes.

In still a further example, aspects of the present invention may be used in connection with building a machine. More particularly, with the development of the 3D-scanner, more and more 3D-models are available. These 3-D models could be used as a training corpus. The question posed by the end user, and understood by the natural language processing engine, could be about a new object, useful for a specific task. For example, the query could be "Build me a new flying vehicle." The model, which has been trained with 3D-models components of cars, boats, and planes, understands from the input that "wings" are essential, as the most significant part used in flying vehicle. A sequence of parts' categories would include the following:

Category 1: Propulsion
Category 2: Flying part
Category 3: Cockpit
Category 4: . . .
Category X: Wings Parts of each category will be selected, fitting constructions constraints. For example, a nuclear propulsion will be hard to fit on a bi-jet cabin. Sequences of compatible parts will be ranked, building a logical flying vehicle. Filtering may also be used, e.g., based on fuel consumption, weight, etc., and the best machine that fits the inquiry could be built. It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed is:

1. A system for designing pipelines using artificial intelligence, comprising:
   an input module that receives input data comprising an inquiry associated with accomplishing a task;
   a model module that receives the input data and executes an artificial intelligence algorithm to design at least one pipeline comprising a plurality of components designed to accomplish the task; a compatibility module that determines at least one valid pipeline by analyzing the at least one pipeline and determining whether each one of the plurality of components are compatible with a component immediately before and a component immediately after the one of the plurality of components; and
   a display module that generates user interface data usable for rendering a display of the at least one valid pipeline.

2. The system of claim 1, wherein the model module identifies at least two pipelines, the compatibility module determines at least two valid pipelines, and wherein one of the at least two valid pipelines is automatically selected and displayed via the display module.

3. The system of claim 1, wherein the model module identifies at least two pipelines, the system further comprising:
   a ranking module that ranks the at least two pipelines based on filtering criteria.

4. The system of claim 1, further comprising:
   a filtering module that filters components of the at least one valid pipeline based on filtering criteria.

5. The system of claim 1, wherein the model module comprises a neural network trained using a pipeline corpus.

6. The system of claim 5, wherein an end user selects one of the at least one valid pipelines and said selection is used to train the model module.

7. The system of claim 1, wherein the input data is processed using the input module using natural language processing.

8. The system of claim 1, wherein the input module comprises a chatbox comprising a model based on a recurrent neural network.

9. The system of claim 1, wherein the task is to perform a bioinformatics analysis.

10. The system of claim 9, wherein the components comprise software tools, each software tool having an input format and an output format, and wherein the at least one valid pipeline is determined by analyzing compatibility of the input format of a tool with the output format of the immediately preceding tool in the at least one valid pipeline.

11. The system of claim 10, wherein, if the input format is not compatible with the output format, the system selects a converter tool to convert one or both of the input format and the output format.

12. The system of claim 1, further comprising:
   an ontology-based validation module that analyzes the plurality of components and (i) accepts the at least one pipeline as a valid pipeline, (ii) rejects the at least one pipeline as a valid pipeline, or (iii) re-orders the components in the at least one pipeline to create a valid pipeline.

13. A computer implemented method for designing pipelines using artificial intelligence, comprising:
   receiving, at an input module, input data comprising an inquiry associated with accomplishing a task;
   receiving, at a model module, the input data and executing an artificial intelligence algorithm to design at least one pipeline comprising a plurality of components designed to accomplish the task;
   determining, using a compatibility module, at least one valid pipeline by analyzing the at least one pipeline and determining whether each one of the plurality of components is compatible with a component immediately before and a component immediately after the one of the plurality of components; and
   displaying using a display module the at least one valid pipeline.

14. The computer implemented method of claim 13, wherein the model module identifies at least two pipelines, the compatibility module determines at least two valid pipelines, and wherein one of the at least two valid pipelines is automatically selected and displayed via the display module.

15. The computer implemented method of claim 13, wherein the model module identifies at least two pipelines and ranks the at least two pipelines based on filtering criteria.

16. The computer implemented method of claim 13, further comprising:
   filtering components of the at least one valid pipeline based on filtering criteria using a filtering model.

17. The computer implemented method of claim 13, wherein the model module comprises a neural network trained using a pipeline corpus.

18. The computer implemented method of claim 17, wherein an end user selects one of the at least one valid pipelines and said selection is used to train the model module.

19. The computer implemented method of claim 13, wherein the input data is processed using the input module using natural language processing.

20. The computer implemented method of claim 13, wherein the input module comprises a chatbox comprising a model based on a recurrent neural network.

21. The computer implemented method of claim 13, wherein the task is to perform a bioinformatics analysis.

22. The computer implemented method of claim 21, wherein the components comprise software tools, each software tool having an input format and an output format, and wherein the at least one valid pipeline is determined by analyzing compatibility of the input format of a tool with the output format of the immediately preceding tool in the at least one valid pipeline.

23. The computer implemented method of claim 22, further comprising, if the input format is not compatible with the output format, selecting a converter tool to convert one or both of the input format and the output format.

24. The computer implemented method of claim 22, further comprising:
   analyzing by an ontology-based validation module the plurality of components and (i) accepting the at least one pipeline as a valid pipeline, (ii) rejecting the at least one pipeline as a valid pipeline, or (iii) re-ordering the components in the at least one pipeline to create a valid pipeline.

* * * * *